Jan. 18, 1966 T. GREEN Plant Pat. 2,587
BOUGAINVILLEA PLANT
Filed Oct. 29, 1964
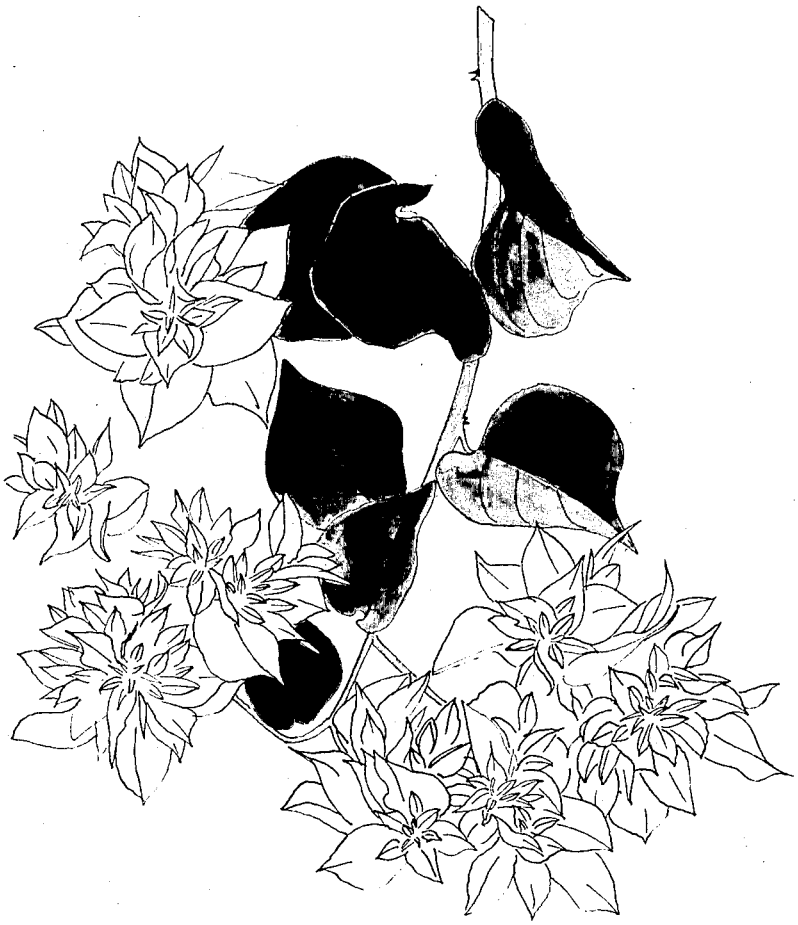
Ted Green United States Patent Office Plant Pat. 2,587
Patented Jan. 18, 1966

2,587
BOUGAINVILLEA PLANT

Ted Green, Honolulu, Hawaii, assignor to Friend of Foster Garden, Inc., Honolulu, Hawaii Filed Oct. 29, 1964, Ser. No. 407,607
1 Claim. (Cl. Plt.—54)

The present discovery relates to a new and distinct variety of Bougainvillea plant, the original of which was a sport discovered by me in the Philippine Islands in a cultivated area.

The original sport was a mutant branch on *Bougainvillea spectabilis* var. *Carmencita,* and differs from the parent by having bracts that are consistently a bronze-pink color. This color can best be described as Marigold Orange 11/2 for new bracts and changing to Mandarin Red 17/3 for older bracts (Royal Horticultural Colour Chart). Occasionally one bract or a portion of a bract is the color of the parent—Rose Bengal 25/1. (See accompanying drawing).

I now have five of these plants which are asexual reproductions made by air-layering. All propagants demonstrate the same character as the original sport.

I claim:

A new and distinct variety of Bougainvillea plant, characterized as to novelty by the tripling of the bracts and the unusual bronze-pink color of the bracts, substantially as shown and described.

No references cited.

ABRAHAM G. STONE, *Primary Examiner.*
R. E. BAGWILL, *Ass't. Examiner.*